United States Patent
Ibsen et al.

(10) Patent No.: US 6,511,654 B2
(45) Date of Patent: Jan. 28, 2003

(54) STARCH THICKENED NON-AQUEOUS DENTIFRICES

(75) Inventors: Robert Ibsen, Santa Maria, CA (US); Rachel R. Pineda, Santa Maria, CA (US); Thomas C. Chadwick, Nipomo, CA (US); Alan Matthews, Santa Maria, CA (US)

(73) Assignee: Den-Mat Corporation, Santa Maria, CA (US)

( * ) Notice: Subject to any disclaimer, the term of this patent is extended or adjusted under 35 U.S.C. 154(b) by 0 days.

(21) Appl. No.: 09/740,982

(22) Filed: Dec. 21, 2000

(65) Prior Publication Data

US 2002/0006386 A1 Jan. 17, 2002

Related U.S. Application Data

(60) Provisional application No. 60/171,596, filed on Dec. 23, 1999.

(51) Int. Cl.[7] .............................. A61K 7/16; A61K 7/18; A61K 7/20; A61K 7/28
(52) U.S. Cl. .............................. 424/49; 424/52; 424/53; 424/50
(58) Field of Search ...................................... 424/49–58

(56) References Cited

U.S. PATENT DOCUMENTS

| | | | | |
|---|---|---|---|---|
| 3,574,824 A | * | 4/1971 | Echeandia et al. ............ 424/50 |
| 3,939,261 A | | 2/1976 | Barth | |
| 4,071,615 A | | 1/1978 | Barth | |
| 4,132,771 A | | 1/1979 | Schreiber et al. | |
| 4,159,316 A | | 6/1979 | Januszewaki et al. | |
| 4,170,635 A | | 10/1979 | Barth | |
| 4,187,287 A | | 2/1980 | Schreiber et al. | |
| 4,391,836 A | * | 7/1983 | Chiu .......................... 426/578 |
| 4,582,701 A | | 4/1986 | Piechota, Jr. | |
| 4,627,451 A | | 12/1986 | Chang | |
| 4,812,306 A | * | 3/1989 | Cochorell et al. ............ 424/52 |
| 4,818,518 A | | 4/1989 | Gioffre et al. | |
| 4,837,008 A | * | 6/1989 | Rudy et al. ................... 424/53 |
| 4,891,211 A | * | 1/1990 | Winston ....................... 424/52 |
| 4,971,782 A | * | 11/1990 | Rudy et al. ................... 424/53 |
| 4,986,981 A | * | 1/1991 | Grace et al. .................. 424/50 |
| 5,004,596 A | * | 4/1991 | Cocherell et al. ............. 424/52 |
| 5,084,268 A | * | 1/1992 | Thaler ......................... 424/53 |
| 5,133,953 A | * | 7/1992 | Kasica et al. ................. 127/65 |
| 5,188,674 A | * | 2/1993 | Kasica et al. ................. 127/65 |
| 5,208,010 A | * | 5/1993 | Thaler ......................... 424/53 |
| 5,614,174 A | * | 3/1997 | Hsu et al. ..................... 424/49 |
| 5,624,612 A | * | 4/1997 | Sewall et al. ................. 264/4.1 |
| 5,670,137 A | | 9/1997 | Ascione | |
| 5,690,913 A | * | 11/1997 | Hsu et al. ..................... 424/53 |
| 5,718,770 A | * | 2/1998 | Shah et al. ................... 127/65 |
| 5,718,969 A | * | 2/1998 | Sewall et al. ............. 428/304.1 |
| 5,720,822 A | * | 2/1998 | Jeffcoat et al. ............... 127/65 |
| 5,725,676 A | * | 3/1998 | Chiu .......................... 127/34 |
| 5,747,005 A | | 5/1998 | Barels et al. | |
| 5,830,884 A | * | 11/1998 | Kasica et al. ............... 514/160 |
| 5,853,050 A | * | 12/1998 | Kittle .......................... 169/47 |
| 5,871,756 A | * | 2/1999 | Jeffcoat et al. ............. 424/401 |
| 5,932,017 A | * | 8/1999 | Chiu .......................... 127/67 |
| 6,010,574 A | * | 1/2000 | Jeffcoat et al. ............... 127/65 |
| 6,248,338 B1 | * | 6/2001 | Muller et al. ............... 424/401 |
| 6,331,291 B1 | * | 12/2001 | Grace et al. .................. 424/49 |

* cited by examiner

*Primary Examiner*—Shep K. Rose
(74) *Attorney, Agent, or Firm*—Dorsey & Whitney, LLP

(57) ABSTRACT

The instant invention relates to an anhydrous dentifrice (toothpaste, brushing gel, etc . . . ) The dentifrice is a homogeneous mixture of the following compounds: (1) organic polyols, such as glycerin; (2) cooked starch gelling agents; (3) mildly abrasive fillers such as silica, alumina and dicalcium phosphate; and, optionally, (4) compounds selected from the group consisting of anti-caries agents, anti-plaque agents, anti-calculus agents, bleaching agents, peroxide stabilizers, desensitizing agents, whiteners, anti-stain agents, breath fresheners, flavorants, sweeteners, colorants, buffers, surfactants, and anti-bacterial agents, with the proviso that if bleaching agents are employed then peroxide stabilizers must also be employed. Preferably, the dentifrice does not contain any gelling agent other than the cooked starch particles.

20 Claims, No Drawings

STARCH THICKENED NON-AQUEOUS DENTIFRICES

This application claims the benefit of Provisional application Ser. No. 60/171,596, filed Dec. 23, 1999, now abandoned.

TECHNICAL FIELD

The instant invention is directed to a dentifrice (toothpaste, brushing gel, etc ... ). More specifically, the instant invention is directed to an anhydrous dentifrice that is thickened with cooked starch.

BACKGROUND ART

Dentifrices are used to clean, bleach, whiten, and otherwise treat the teeth and gums. Generally, the active ingredients in a dentifrice are contained within a carrier.

The carrier is either a paste (i.e., toothpaste) or a gel (i.e., brushing gels and bleaching gels). Each is dispensed through a tubular orifice onto a brushing device or, in some cases, onto a tray, stint or mouth guard. "Gels" are thickened by a gelling agent that hydrogen bonds a dispersion medium to produce a semisolid, transparent, jelly-like, material. In contrast, "pastes" are thickened by the addition of fillers. However, the line between gels and pastes is not always clear. Furthermore, sometimes dentifrices that are opaque and/or contain one or more abrasive fillers are labeled pastes, even if they exhibit gel-like properties. Therefore, in describing the present invention, the term "dentifrice" will be used to clearly indicate that both gels and pastes are embraced.

The efficacy of a dentifrice is directly proportional to the time the active ingredients contact the teeth and gums (a.k.a. "the residence time"). If the dentifrice disintegrates immediately upon contact with saliva, or brushing, then it will provide minimal benefit. In contrast, if the dentifrice does not readily disintegrate, it is much more effective.

Usually, the carrier for the active ingredients in the dentifrice contains water as the principal component. However, the use of water has several disadvantages. First, there are numerous beneficial materials that have limited solubility in, or even react with, aqueous systems. Second, water based dentifrices rapidly disintegrate in the presence of saliva since water is a principle component in saliva.

One method of improving residence time has been to utilize anhydrous compositions. These compositions often utilize oils or organic polyols as the principal carrier. Examples of anhydrous dentifrices include the following U.S. Pat. Nos. 3,939,261; 4,071,615; 4,132,771; 4,159,316; 4,170,635; 4,187,287; 4,582,701; 4,627,451; 4,812,306; 4,818,518; 5,670,137; and 5,747,005. These compositions suffer from a number of problems, one of the most common being a failure to provide adequate viscosity and tack.

The efficacy of a dentifrice is highly dependent upon obtaining an acceptable level of viscosity (flow resistance) and tack (adhesion). If the viscosity is too low, the composition is runny and hard to control. On the other hand, if the composition is too viscous it becomes difficult to expel from the tube. Similarly, if the composition is too tacky it leaves a stringy tail as it issues from the tube. But if the composition is not sufficiently tacky it fails to adequately adhere to the treated surfaces of the teeth and gums.

It is difficult to fine tune the viscosity of a dentifrice. This is especially true when the dentifrice exhibits gel-like qualities. This is because the degree of hydrogen bonding interaction between the gelling aid and the dispersion medium is complex and hard to manipulate. Furthermore, for reasons that are not fully understood, gels are susceptible to viscosity increases and decreases over time.

Starch is not a common ingredient in dentifrices. When starch is employed, it is generally as a filler rather than as a gelling agent. It is not believed that the benefits of using cooked starch as a gelling aid in dentifrices have been previously recognized.

U.S. Pat. Nos. 5,084,268 and 5,208,010 ("the Thaler patents") describe an abrasive free hydrogen peroxide tooth whitening dentifrice composition that comprises a blend of corn starch, sorbitol, hydrogen peroxide, carbomer 940, flavor, sodium lauryl sulfate, sodium saccharin, potassium sorbate, and sodium benzoate in an aqueous base. The "[c]orn starch . . . functions as a gelling agent, a thickener, a filler and a binder." A commercial product that is allegedly based on these patents is called "Booster" and is sold by Dental Concepts Inc. of Elmsford, N.Y.

The dentifrice described in the Thaler patents is water based-containing anywhere from 30.65% to 61.65%, by weight, water. As stated, water based dentifrices generally exhibit inferior residence time. Furthermore, the predominant gelling agent in the composition described in the Thaler patents is a carbomer even though the starch is described as both a filler and a gelling agent. In truth, the composition described in the Thaler patents utilize starch more as a filler. Based on prior experience with other formulations, it is believed that a combination of carbomer and starch means that the material will harden during storage. Finally, the Thaler patents fail to recognize that cooked starch provides far greater gelling action than uncooked starch and, therefore, far greater thickening action.

U.S. Pat. Nos. 4,812,306 and 5,004,596 ("the Cocherell patents") describe a water free oil based dentifrice that comprises hydrogenated vegetable oils, flavoring oils, glycerin, cornstarch, inorganic salts, fluorides, saccharin or aspartame, and sodium lauryl sulfate. The cornstarch is added to thicken the mixture into a dough-like mass that is dried, ground, and mixed into the oil to form a cream or paste.

It is important to understand that the composition described in the Cocherell patents, although anhydrous, utilizes oils as the primary carrier rather than organic polyols. Glycerin, although present, makes up only 11.65%, by weight, of the composition whereas various oils make up more than 46% of the composition. Furthermore, although the composition employs starch as thickening agent, the thickening action obtained is no more than would be obtained using any solid filler. The Cocherell patents do not recognize that cooking increases the gelling action, and therefore the thickening action, of starch.

The closest prior art to the instant invention is U.S. patent application Ser. No.08/640,350 ("the '350 application"). This application describes some of Den-Mat Corporation's previous research in anhydrous, polyol based, dentifrices. The dentifrice described in the '350 application utilizes glycerin as a dispersion medium, carbomer (neutralized polyacrylic acid salt) as a gelling agent, peroxide as a bleaching agent, Citroxain® (a mixture of papain, citric acid and its salts, and hydrated alumina) for whitening, dicalcium phosphate as a mild abrasive filler, and uncooked starch thickeners. The dentifrice described in the '350 application demonstrates a number of desirable attributes—such as consistency, feel, cleaning, whitening, and bleaching capabilities. Unfortunately, the dentifrice also exhibits features that have proven to be undesirable. Paramount among the detrimental properties is a tendency to harden within the tube over a relatively short period of time (1 to 2 months) at rather moderate temperatures (~30° C.). The dentifrice also exhibits a tendency to evolve oxygen gas. Oxygen evolution starts immediately after the product is prepared. The formation of oxygen within the tube causes the product to self-extrude from open tubes and swell and/or rupture closed tubes.

Hardening can be slowed by adding more glycerin. However, this also causes a dramatic and undesirable reduction in viscosity. Furthermore, the use of additional glycerin only delays, and does not prevent, the onset of hardening. Dilution of the formulation does not improve the gas evolution problem.

Some, or all, of these problems can be prevented by eliminating one or more of the starch, dicalcium phosphate, or carbomer components. However, once again, such formulations do not possess desirable viscosity characteristics.

Thus there is still a need in the art for new and improved anhydrous dentifrice formulations. Such formulations should be stable, tacky, glossy, smooth flowing, thixotropic, and exhibit high residence time.

SUMMARY OF THE INVENTION

The instant invention relates to an anhydrous dentifrice. The dentifrice is a stable, tacky, glossy, smooth flowing, thixotropic, organic polyol-based material that exhibits high residence time. The dentifrice is made from a homogeneous mixture of the following compounds: (1) low molecular weight organic polyols; (2) a gelling agent comprising cooked starch particles; (3) mildly abrasive fillers; and, optionally, (4) one or more compounds selected from the group consisting of anti-caries agents, anti-plaque agents, anti-calculus agents, bleaching agents, peroxide stabilizers, desensitizing agents, whiteners, anti-stain agents, breath fresheners, flavorants, sweeteners, colorants, buffers, surfactants, and anti-bacterial agents, with the proviso that if bleaching agents are employed then peroxide stabilizers must also be employed. Preferably, the cooked starch particles are the only gelling agent in the dentifrice.

The dentifrice exhibits many advantageous properties Among these is the ability to maintain its viscosity over an extended period of time. This is true even when the paste is heated to 45° C. (113° F.). Thus, unlike previous products, the dentifrice does not harden within the tube during storage. Furthermore, the dentifrice exhibits a reduced tendency to evolve oxygen when peroxide bleaching agents are present. This is important because oxygen evolution causes many products to swell and/or rupture closed tubes during storage and self-extrude from open tubes during use.

DISCLOSURE OF THE INVENTION

As stated, the instant invention relates to an anhydrous dentifrice. The dentifrice is a stable, tacky, glossy, smooth flowing, thixotropic, organic polyol-based material that exhibits high residence time.

By "anhydrous" it is meant that water is never deliberately added in and of itself and is not one of the principal components of the invention. However, the term "anhydrous" does not mean that small amounts of water cannot be present. For the purposes of this invention, "anhydrous" should be interpreted to mean that water is not present in an amount greater than 3% of the total weight of the dentifrice.

By "stable" it is meant that the dentifrice exhibits a shelf-life of at least 36 months when stored at temperatures at or below approximately 30° C. Unlike many products, the instant dentifrice is easily dispensed from a standard toothpaste tube under the aforementioned storage conditions and time parameters. In addition, the term "stable" signifies that the dentifrice may contain up to 10% carbamide peroxide without generating sufficient oxygen to rupture a standard unopened toothpaste tube during the afore mentioned storage conditions and time parameters.

By "tacky" it is meant that the dentifrice forms a sticky film when applied to the teeth and gums that is able to withstand the brushing action of a toothbrush. This is important because the utility of a dentifrice is, in part, dependant upon its residence time. The residence time being defined herein as the time the dentifrice actually contacts the teeth and gums.

By "glossy" it is meant that the dentifrice exhibits a high surface gloss when it is freshly dispensed.

By "smooth flowing" it is meant that the dentifrice has a viscosity between 30,000 cps and 150,000 cps as measured by a Brookfield Model DV-II and a Model 91 T-bar Spindle. Such viscosities make it easy to squeeze the dentifrice from the tube onto the toothbrush.

By "thixotropic" it is meant that the composition partially or fully liquifies when agitated and returns to a gel-like state when at rest. A thixotropic dentifrice flows easily when pressure is applied and exhibits a non-runny consistency when pressure is released. Thixotropy permits the dentifrice to be easily and cleanly cut after the desired amount of dentifrice has been extruded. Thixotropic materials also exhibit increased residence time.

By "organic polyol-based" it is meant that the dentifrice is not oil-based or water-based. Instead, organic polyols are a principal component in the system and, when taken together, make up a higher portion of the system's weight than any other compound except, possibly, filler.

By "high residence time" it is meant that the dentifrice exhibits sufficient film integrity to avoid disintegrating immediately upon exposure to water (a major component of saliva) but incrementally disperses upon contact with water. In other words, the solubility of the dentifrice is a balance between the need to readily dissolve by natural means (saliva) and the need to have sufficient residence time to actually treat the teeth.

The first component of the dentifrice is one or more low molecular weight organic polyols. The organic polyols are humectant materials that create a dispersion medium for the dentifrice. The molecular weight of the organic polyols employed should not exceed 182.

Preferred organic polyols are selected from ethylene glycol, glycerin, propylene glycol, xylitol, sorbitol, mannitol, lactitol, maltitol, erythritol, and mixtures thereof. Specific organic polyols, or mixtures, that have proved especially advantageous are glycerin, glycerin-propylene glycol mixtures, xylitol-glycerin mixtures, sorbitol-glycerin mixtures, mannitol-glycerin mixtures, lactitol-glycerin mixtures, maltitol-glycerin mixtures, and erythritol mixtures.

Glycerin is the most preferred organic polyol. Glycerin, also known by the names glycerol, glycyl alcohol, 1,2,3-propanetriol, and trihydroxypropane, is a commercially available trihydric alcohol. Pure anhydrous glycerin can be obtained and is preferred. However, it is recognized that commercially available glycerin often contains up to 2.0%, by weight, water. Although it is preferred to use glycerin that contains no water, this small amount of water is not detrimental to the invention because it is in association with (bound to) the glycerin and, therefore, is not available for interaction with the other ingredients in the dentifrice.

The sum total of the organic polyols used in the invention constitute from 30% to 85% of the total weight of the dentifrice. Preferably, the organic polyols represent from 40% to 70% of the total weight.

Dispersed within the dispersion medium of organic polyols are starch particles. Starches are reserve polysaccharides found in plants, such as corn, potatoes, tapioca, rice, and wheat. They are generally composed of about 20 to 40 weight percent amylose and 60 to 80 weight percent amylopectin. For example, cornstarch is a specific starch that is composed of about 20 to 25% amylose and about 75 to 80% amylopectin. Amylose and amylopectin are classified as homopolysaccharides. These polymers have molecular weights in the range of about 150,000 to about 600,000 (Morrison and Boyd, *Organic Chemistry*, Fifth Edition, 1987, p. 1333).

Modified starches can also be used. For example, it is well known to acylate amylopectin and amylose. Acylation is commonly carried out by reacting amylopectin and/or amylose with an organic carboxylic acid or anhydride in the presence of an acid or basic catalyst.

The starch particles must be cooked. This is acritical feature of the invention. By "cooked" it is meant that the particles are treated with heat. Heat treatment causes the starch's polymer chains to disentangle and occupy more space, which results in an observable swelling ofthe particles. Because the polymer chains disentangle and occupy more space, they are better able to generate the hydrogen bonds necessary to gel the dispersion medium. Properly cooked (swelled) particles are not birefringent and, typically, at least some of the boundaries in the particles become indistinct. Starch particles that are not cooked exhibit little or no gelling action. Uncooked starches may thicken the material but the effect is no greater than that which one would expect from the inclusion of any solid filler.

Cooking can be done after the starch is added to the organic polyol dispersion. Preferably, partially pre-cooked starches are added to the dispersion and then the system is heated to fully cook the starches. Partially pre-cooked starches are called "cold cooked" starches. As the name "cold cook" implies, these partially pre-cooked starches require lower cook times and temperatures (generally from about 80° C. to about 140° C.). Thus, cold cook starches place fewer demands on processing equipment. However, other starches, whether partially precooked or not, may be utilized. The maximum cooking temperature for most starches is about 160° C. and, depending on the starch, takes anywhere from several minutes to several hours.

Stirring is not necessary to achieve gelation. However, a better gel results if the starch grains are suspended during cooking. Therefore, some agitation, while not absolutely necessary, is desirable.

The uncooked starch particles generally have a mean diameter of from 5 to 20 microns prior to cooking. Preferably, the particles have a mean diameter of around 10 to 15 microns prior to cooking. When the particles are properly cooked, the diameter swells at least about three fold.

The cooked starches constitute from 1% to 20% of the total weight of the dentifrice. Preferably, the cooked starches make up 3.5% to 10% of the total weight.

Substitution, or even the additional inclusion, of any other type of gelling agent besides the "cooked" starches may result in a hardening of the dentifrice during storage. This is especially true when carbomer (neutralized polycarboxylic acid salt) gelling agents are added—such as the carbomers sold by B. F. Goodrich Company under the Carbopol™ label. Hardening is undesirable because it makes it more difficult, and sometimes nearly impossible, to squeeze the dentifrice out of the tube.

In addition, the preparation of desensitizing compositions is difficult using polyacrylic acid based gelling agents because desensitizing agents are generally ionic compounds such as potassium salts (the most prevalent being potassium nitrate). High concentrations of ionic compounds adversely affect the performance of polycarboxylic acid gelling agents which are ionic in nature. Specifically, combining a carbomer with large amounts of electrolytes makes the system runny. In contrast, starches are neutral molecules and are much less affected by high concentrations of salts.

The third component of the dentifrice is a heterogeneous mixture of one or more mildly abrasive fillers. Preferred abrasives are insoluble materials such as silica, alumina, dicalcium phosphate, tetrasodium pyrophosphate, calcium carbonate, and mixtures thereof. It is, in part, the mildly abrasive nature of these fillers that removes plaque, calculus, and stains from the teeth during brushing. The most preferred abrasive filler is dicalcium phosphate since it serves as both a mild abrasive and a calcium source for remineralization.

The abrasive fillers make up 1% to 60% of the total weight of the dentifrice. Preferably, the abrasive fillers constitute from 15% to 50% of the total weight.

Finally, a number of optional components may be included in the dentifrice. These optional components may be dissolved or suspended in the dentifrice and are selected from the group consisting of anti-caries agents, anti-plaque agents, anti-calculus agents, bleaching agents, peroxide stabilizers, desensitizing agents, whiteners, anti-stain agents, breath fresheners, flavorants, sweeteners, colorants, buffers, surfactants, preservatives, and anti-bacterial agents.

Anti-caries agents help prevent cavities by strengthening the teeth. The preferred anti-caries agents are fluoride sources. Preferred fluoride sources are alkali metal fluorides and alkali metal monofluorophosphates, especially sodium fluoride and sodium monofluorophosphate. Stannous fluoride, which is not used in conventional dentifrice formulations owing to its instability in an aqueous environment, may also be used.

The anti-caries agents should be present in an amount no greater than 1500 ppm (asF) of the total weight of the dentifrice. Preferably, anti-caries agents make up 850 ppm (asF) to 1500 ppm (asF) of the total weight.

Anti-plaque agents remove and/or prevent plaque build-up on the teeth. Suitable anti-plaque agents include triclosan, chlorhexidine, cetyl pyridinium chloride and nicin (preferably in a purified form, and available as Ambicin N).

Anti-calculus agents remove the build-up of mineral salts from the teeth. Suitable anti-calculus agents include pyrophosphate salts.

Bleaching agents serve to whiten the teeth by reacting with, and breaking down, stain forming materials. Preferred bleaching agents are peroxides, such as hydrogen peroxide ($H_2O_2$) and any compound that yields hydrogen peroxide when placed in an aqueous medium (such as the aqueous environment found inside the mouth). In example, urea peroxide ($CO(NH_2)_2H_2O_2$) generates hydrogen peroxide when placed in water. Other names for urea peroxide include carbamide peroxide, urea hydrogen peroxide, hydrogen peroxide carbamide and perhydrol urea. Generally, urea peroxide is preferred because it adds peroxide to the formulation without adding water and is easy to store and use.

The bleaching agents should constitute no more than 10% of the total weight of the dentifrice. A higher concentration of bleaching agent tends to irritate gums and other oral tissue. Preferably, bleaching agents represent from 0% to 10% of the total weight.

If peroxides are utilized then it is an additional requirement of the invention to also utilize peroxide stabilizers. Otherwise, the dentifrice will burst despite its increased resistance to oxygen evolution. Such stabilizers include amino carboxylic acids and salts thereof. Preferred stabilizers are selected from aminocarboxylic acids and alkali and/or alkali earth metal salts thereof. Suitable aminocarboxylic acids include trans-1,2-cyclohexylene dinitrilotetraacetic acid (CDTA), ethylenediamine tetraacetic acid (EDTA), N—(2-hydroxyethyl) ethylenediamine triacetic acid (HEDTA), Nitrilotriacetic acid (NTA), diethylene triamine pentaacetic acid (DTPA), triethylene tetraamine hexaacetic acid (TTHA), and ethyleneglycol bis (2-aminoethylether) tetraacetic acid (GEDTA). The most preferred stabilizers include CDTA, $CaNa_2EDTA$, $Na_2EDTA$, $Na_4EDTA$, HEDTA, and $Na_3HEDTA$.

The peroxide stabilizers should constitute no more than 0.25% of the total weight of the dentifrice. Preferably, the peroxide stabilizers make up 0.05% to 0.15% of the total weight.

It may be desirable to incorporate one or more desensitizing agents into the dentifrice, especially when glycerin is selected as the organic polyol and/or a peroxide bleaching agent is employed. Preferred desensitizing agents include alkali and alkaline earth metal salts of organic and inorganic acids and halides. These compounds significantly reduce, or completely remove, any sensitivity that may occur in the teeth and other oral tissue by glycerin and/or the peroxide bleaching agents. However, these compounds do not hinder the stability of the dentifrice. Preferably, the desensitizing agents are selected from the group consisting of alkali and alkaline earth metal salts of nitric acid, citric acid, and halides. Specific examples of suitable desensitizing agents include potassium nitrate, potassium citrate, strontium nitrate and strontium chloride. The most preferred desensitizing agent is potassium nitrate due to its effectiveness and approval by the United States Food and Drug Administration ("USFDA"). The desensitizing agents make up no more than 5% of the total weight of the dentifrice. The USFDA currently sets the amount of densensitizing agent in dentifrices at 5% of the total weight.

The whitening agent employed in this formulation is Citroxain® which is a combination of citric acid and its salts, aluminum oxide and papain).

The whitening agents should constitute no more than 16.4% of the total weight of the dentifrice. Preferably, whitening agents make up 5.8% to 16.4% of the total weight.

Dentifrices according to the invention may also contain an anti-stain agent. Suitable anti-stain agents include, for example, carboxylic acids such as those disclosed in U.S. Pat. No. 4,256,73 1, amino carboxylate compounds such as those disclosed in U.S. Pat. No. 4,080,441 and phosphonoacetic acid, as disclosed in U.S. Pat. No. 4,118,474.

Breath freshening agents remove malodors from the mouth. Suitable breath freshening agents include zinc salts, chlorophyll, and chlorate salts.

Flavoring agents may be used to improve the taste of the dentifrice. Preferred flavoring agents include cinnamon, cassia, anise, menthol, methyl salicylate, peppermint oil, spearmint oil, and other known flavor modifiers.

When flavoring agents are utilized, they make up no more than 1.5% of the total weight of the dentifrice. Preferably, flavoring agents are employed in an amount ranging from 0.2% to 1.5% of the total weight.

In addition to the flavoring agents natural or artificial sweeteners such as sorbitol, xylitol, aspartame, and sodium saccharin may be used. These components, like flavorants, improve the taste of the composition.

Colorants maybe added to increase the aesthetic appeal of the dentifrice. Consumers tend to purchase products that appear, based on their color, to be natural or sterile (e.g., blue, white, and/or green). Any FDA approved food colorant may be utilized.

When colorants are utilized, they make up no more than 0.1% ofthe total weight ofthe dentifrice. Preferably, colorants employed in an amount ranging from 0.001% to 0.05% of the total weight.

Buffering agents are sometimes included to adjust the pH ofthe final formulation. Generally, any buffering agent maybe used that is capable of bringing the pH ofthe dentifrice to a physiologically acceptable level and that is approved for use in food products. For a dentifrice, the pH ofthe material should be between 5.6 and 9. Preferably, the pH is around 6.5. Exemplary buffering agents are alkali metal and alkaline earth metal salts and amine (e.g., ammonium) salts of weak carboxylic acids. The preferred buffering agents are sodium citrate, potassium citrate, and sodium acetate.

The buffering agents should represent no more than 5% ofthe total weight ofthe dentifrice. Preferably, the buffering agents are present in an amount ranging from 0.5% to 3.0% ofthe total weight.

Surfactants may be included emulsify flavors, improve mouth feel and add foam. Any food grade anionic, cationic, non-ionic and amphoteric surfactants surfactant can be employed.

Surfactants should represent no more than 5% ofthe total weight of the dentifrice. Preferably, the surfactants represent 0.5% to 3.5% of the total weight.

Antibacterial agents may also be used. A combination of sodium benzoate and a weak carboxylic acid has been found to exhibit antibacterial properties. Additional antibacterial agents include phenolic compounds such as β-naphthol, thymol, chlorothymol, amyl-, hexyl-, heptyl- and octylphenol, hexylresorcinol, hexachlorophene, and phenol; quarternary ammonium compounds such as quarternary morpholinium alkyl sulfates, cetylpyridinium chloride, alkyldimethyl benzylammonium chloride, and alkyltrimethyl ammonium halides. In addition, miscellaneous antibacterial compounds may be employed such as benzoic acid, potassium chlorate, tyrothricin, gramicidin, iodine, sodium perborate, and urea peroxide. The amount of anti-bacterial agent that may be added obviously varies depending on the particular agent.

Preferably, the dentifrice corresponds to the formulation set forth in the following table:

TABLE 1

| Ingredient Types | (%) |
| --- | --- |
| Organic polyol(s) | 30.0–85.0 |
| Buffering agent(s) | 0.5–10.0 |

TABLE 1-continued

| Ingredient Types | (%) |
| --- | --- |
| Bleaching agent(s) | 0.1–10.0 |
| Sweetener(s) | 0.01–20.0 |
| Fluoride ion source | 0.15 |
| Surfactant(s) | 0.5–5.0 |
| Abrasive filler(s) | 1.0–60.0 |
| Papain | 0.25–0.8 |
| Desensitizer | 5.00 |
| Flavorants | 0.5–1.5 |
| Peroxide stabilizer | 0.05–0.15 |
| Starch | 3.5–10.0 |

More preferably, the dentifrice corresponds to the formulation described in the following table:

TABLE 2

| Ingredient Types | (%) |
| --- | --- |
| Glycerin 99.7% USP | 50.04 |
| Sodium Citrate | 2.37 |
| Carbamide Peroxide | 7.00 |
| Sodium Saccharin | 0.11 |
| Sodium Monofluorophosphate | 0.88 |
| Citric Acid | 0.48 |
| Sodium Lauryl Sulfate | 1.00 |
| Silica | 14.80 |
| Alumina | 3.35 |
| Dicalcium Phosphate | 8.10 |
| Papain | 0.68 |
| Potassium Nitrate | 5.00 |
| Flavor | 1.10 |

TABLE 2-continued

| Ingredient Types | (%) |
| --- | --- |
| Calcium disodium EDTA | 0.09 |
| Starch | 5.00 |
| Total | 100.00 |

Generally, the starch-polyol gel is formed prior to the addition of any other components. After the gel has been formed, the remainder of the ingredients are added. This is best accomplished by first adding the most stable compounds of the formulation, such as surfactants, sodium citrate, citric acid, potassium nitrate, sodium saccharin, and disodium calcium EDTA. Next, abrasive fillers, such as silica, dicalcium phosphate, and alumina, are added. Finally, materials of lesser stability or high volatility, such as sodium monofluorophosphate ("MFP"), flavorants, peroxides, and papain or other enzymes, are incorporated into the formulation. It may be desirable to cool the mixture before adding this last group of compounds.

Examples of the inventive dentifrice and its properties are provided below. These examples are for the purpose of illustration and not limitation. Many other embodiments of the invention, that are not specifically set forth in the examples, are both envisioned and embraced.

EXAMPLES 1–9

Nine preparations containing the following components, in the following amounts, were prepared:

TABLE 3

| Example | 1 | 2 | 3 | 4 | 5 | 6 | 7 | 8 | 9 |
| --- | --- | --- | --- | --- | --- | --- | --- | --- | --- |
| Glycerin | 32.81 | 40.71 | 45.02 | 35.71 | 40.02 | 55.04 | 46.52 | 55.04 | 50.04 |
| Sodium Citrate | 2.65 | 2.41 | 2.41 | 2.42 | 2.41 | 2.41 | 2.41 | 2.37 | 2.37 |
| Urea Peroxide | 9.10 | 9.06 | 9.01 | 9.06 | 9.01 | 7.00 | 9.01 | 7.00 | 7.00 |
| Sodium Saccharin | 0.15 | 0.13 | 0.11 | 0.13 | 0.11 | 0.11 | 0.11 | 0.11 | 0.11 |
| Sodium MFP | 0.85 | 0.85 | 0.85 | 0.85 | 0.85 | 0.88 | 0.85 | 0.88 | 0.88 |
| Citric Acid | — | 0.40 | 0.50 | 0.40 | 0.50 | 0.48 | 0.50 | 0.48 | 0.48 |
| SLS | 1.12 | 1.03 | 0.91 | 1.03 | 0.91 | — | 0.91 | 1.00 | 1.00 |
| Sylodent 753 | 13.54 | 19.07 | 15.37 | 19.07 | 15.37 | 14.80 | 15.37 | 14.80 | 14.80 |
| Alumina | 7.35 | — | 3.48 | — | 3.48 | 3.35 | 3.48 | 3.35 | 3.35 |
| DCP | 21.43 | 19.56 | 15.59 | 19.55 | 15.56 | 8.10 | 15.56 | 8.10 | 8.10 |
| Papain | 0.74 | 0.68 | 0.68 | 0.68 | 0.68 | 0.68 | 0.68 | 0.68 | 0.68 |
| $KNO_3$ | — | — | — | — | — | — | — | — | 5.00 |
| Flavor | 1.17 | 1.11 | 1.10 | 1.11 | 1.10 | 1.10 | 1.10 | 1.10 | 1.10 |
| $CaNa_2$-EDTA | — | — | — | — | — | 0.05 | — | 0.09 | 0.09 |
| Polar Tex "Gelex" | — | 5.00 | 5.00 | 10.00 | 10.00 | 5.00 | 3.50 | 5.00 | 5.00 |
| TEGO Betaine CK D | — | — | — | — | — | 1.00 | — | — | — |
| Propylene Glycol | 1.80 | — | — | — | — | — | — | — | — |
| National 4012 | 1.52 | — | — | — | — | — | — | — | — |
| Collo 67 | 5.34 | — | — | — | — | — | — | — | — |
| Carbopol 940 | 0.43 | — | — | — | — | — | — | — | — |
| Total | 100 | 100.01 | 100.03 | 100.01 | 100 | 100 | 100 | 100 | 100 |

Comparative Example 1 is a representative of a previous Den-Mat formulation and is included for the purposes of comparison. Comparative Example 7 utilizes peroxide without peroxide stabilizer. Inventive Examples 2–6 and 8–9 represent different embodiments of the instant invention.

Viscosity Stability

The non-hardening properties of dentifrices made in accordance with the instant invention can be illustrated by a comparative test between Comparative Example 1 and Inventive Examples 2–5. Example 1, as stated, represents a current Den-Mat product that uses un-cooked starches as a filler and Carbopol as a gelling agent. Examples 2–5, as stated, are representative of the invention wherein cooked starches are used as the only gelling agents.

The stability of Example 1 was evaluated at 23° C. (room temperature), 35° C., and 45° C. The stability of Examples 2–5 were evaluated at these same temperatures and, additionally, at 55° C. The results of the test are summarized in the following table:

TABLE 4

| Example | Room Temp. | 35° C. | 45° C. | 55° C. |
| --- | --- | --- | --- | --- |
| 1 | 8 weeks | 4 weeks | (tube burst) | 5 days |
| 2 | >27 weeks | >27 weeks | >27 weeks | — |
| 3 | >27 weeks | >27 weeks | >27 weeks | — |
| 4 | >27 weeks | >27 weeks | >27 weeks | — |
| 5 | >27 weeks | >27 weeks | >27 weeks | — |

As can be seen, Example 1 could not be dispensed after 8 weeks at room temperature, 4 weeks at 35° C., and 5 days at 55° C. The 45° C. sample of Example 1 was not available for evaluation because the tube burst during the incubation. In contrast, the stability of Examples 2–5 remained easy to dispense after 27 weeks storage at all of the testing temperatures.

Peroxide Stability

The improved ability of the inventive dentifrice to resist oxygen gas evolution is demonstrated by comparison between Comparative Examples 1 and 7 with Inventive Example 6. Samples of product were prepared according to each of these formulations. As stated, Comparative Example 1 contains uncooked starch and additional gelling agents and Comparative Example 7 contains peroxide but no peroxide stabilizer. Each sample was packaged in a 4.5 oz polypropylene toothpaste tube and placed in a 45° C. stability cabinet.

Tubes containing Example 1 burst after only 2 weeks of storage. After one month of storage, the tube that contained the composition of Example 7 had swollen nearly to the point of rupture. It had a knot the size of a golfball. Furthermore, the tube expelled a 1–2 in. ribbon of product upon opening.

In contrast, the tube that contained Example 6 expanded only slightly after four months of storage. When the tube was opened, it only expelled a pea sized drop of material

EXAMPLE 10

Preparation of Small Batches

To prepare small batches of the inventive dentifrice, first disperse cold cooked starch into a vessel that contains an organic polyol solvent. Then place the vessel, containing the solvent and starch, into a laboratory oven whose temperature is maintained at 130° C. At 10 minute intervals, check the starch dispersion to see if gelation has taken place. When gelation is complete, remove the vessel from the oven and transfer the contents to the mixing bowl of a Kitchen Aid® benchtop mixer. Allow the contents to cool. Once the gel has reached room temperature, add sodium citrate, citric acid, sodium saccharin, MFP, CaNa$_2$EDTA, potassium nitrate, and sodium lauryl sulfate. Using the Kitchen AID® mixer, mix the contents until a smooth paste, free of undissolved particulate, is obtained. Then add amorphous silica abrasive, alumina, and dicalcium phosphate. Mix until a homogeneous blend is obtained. Finally, incorporate flavor, papain, and urea peroxide. Mix the contents, once again, until the dentifrice is homogeneous.

EXAMPLE 11

Preparation of Large Batches

A large scale batch of the inventive dentifrice was prepared using a Ross 40 gallon stainless steel, vacuum capable, jacketed power mixer equipped with both a disperser and planetary mixer agitators. In a typical preparation, the mixer was first charged with glycerin (~25° C.) and then the starch was added. After starch addition, the contents were mixed with both the disperser and the planetary mixer. Once the starch was fully dispersed, the disperser was turned off and the dispersion was heated to effect gelation. Heating was achieved by circulating a heated mixture of propylene glycol and water through the vessel's heating jacket. After one hour of continuous heating, the starch dispersion was checked for gelation and reevaluated at 15 minute intervals thereafter until gelation was complete. The starch dispersion gelled by the time the mixture reached a temperature of 214° F. Heating was discontinued and chilled heat transfer fluid was circulated through the jacket to cool down the mixer. After cooling for ten minutes, sodium citrate, CaNa$_2$EDTA, citric acid, and sodium lauryl sulfate were added. The composition was then vacuum mixed using both the disperser and planatery mixer until the gel was free of gritty particles. Cooling was continued. Then the contents were mixed under vacuum until the dentifrice was smooth. The mixture was cooled to 97° F. prior to the addition of papain, MFP, sodium saccharin, urea peroxide, and flavor. After the addition was completed, the dentifrice was thoroughly mixed under vacuum until homogeneous. After sampling and testing the batch to establish that design requirements had been met, the product was filled into 4.5 oz. polypropylene toothpaste tubes using typical automated tube filling equipment.

We claim:

1. A stable, tacky, glossy, smooth flowing, thixotropic, organic polyol-based anhydrous dentifrice that exhibits high residence time and comprises a homogeneous mixture of the following components:
   (1) one or more low molecular weight organic polyols;
   (2) one or more gelling agents selected from cooked starch particles;
   (3) one or more mildly abrasive fillers; and, optionally,
   (4) various other compounds selected from the group consisting of anti-caries agents, anti-plaque agents, anti-calculus agents, bleaching agents, peroxide stabilizers, desensitizing agents, whiteners, anti-stain agents, breath fresheners, flavorants, sweeteners, colorants, buffers, surfactants, and anti-bacterial agents, with the proviso that if bleaching agents are employed then peroxide stabilizers must also be employed.

2. The dentifrice of claim 1, wherein the organic polyol is selected from the group consisting of glycerin, propylene glycol, xylitol, sorbitol, mannitol, lactitol, maltitol, erythritol, and mixtures thereof.

3. The dentifrice of claim 1, wherein organic polyols make up from 30 to 85 percent of the total weight of the dentifrice.

4. The dentifrice of claim 1, wherein the mildly abrasive filler is selected from the group consisting of silica, alumina, dicalcium phosphate, calcium carbonate and mixtures thereof.

5. The dentifrice of claim 1, wherein the mildly abrasive filler makes up from 1 to 60 percent of the total weight of the dentifrice.

6. The dentifrice of claim 1, wherein the starch particles contain amylose, amylopectin, acylated amylose, acylated amylopectin, or a mixture thereof.

7. The dentifrice of claim 1, wherein the starch particles are cooked to a point where they cease to birefringent and at least some of the boundaries in the particles become indistinct.

8. The dentifrice of claim 1, wherein cooked starch particles are the only gelling agent employed.

9. The dentifrice of claim 1, wherein cooked starch particles make up from 1 to 20 percent of the total weight of the dentifrice.

10. A dentifrice comprising the following components in the following amounts:

| Ingredient Types | (%) |
| --- | --- |
| Organic polyol(s) | 30.0–85.0 |
| Buffering agent(s) | 0.5–10.0 |
| Bleaching agent(s) | 0.1–10.0 |
| Sweetener(s) | 0.01–20.0 |
| Fluoride ion source | 0.15 |
| Surfactant(s) | 0.5–5.0 |
| Abrasive filler(s) | 1.0–60.0 |
| Papain | 0.25–0.8 |
| Desensitizer | 5.00 |
| Flavorants | 0.5–1.5 |
| Peroxide stabilizer | 0.05–0.15 |
| Cooked Starch | 3.5–10.0. |

11. The dentifrice of claim 10 comprising the following components in the following amounts:

| Ingredient Types | (%) |
| --- | --- |
| Glycerin 99.7% USP | 50.04 |
| Sodium Citrate | 2.37 |
| Carbamide Peroxide | 7.00 |
| Sodium Saccharin | 0.11 |
| Sodium Monofluorophosphate | 0.88 |
| Citric Acid | 0.48 |
| Sodium Lauryl Sulfate | 1.00 |
| Silica | 14.80 |
| Alumina | 3.35 |
| Dicalcium Phosphate | 8.10 |
| Papain | 0.68 |
| Potassium Nitrate | 5.00 |
| Flavor | 1.10 |
| Calcium disodium EDTA | 0.09 |
| Cooked Starch | 5.00 |
| Total | 100.00 |

12. A method of making a dentifrice comprising the following steps:
(i) forming a gel by cooking starch particles in the presence of one or more organic polyols; and
(ii) adding mild abrasives to the gel and, optionally, various other compounds selected from the group consisting of anti-caries agents, anti-plaque agents, anti-calculus agents, bleaching agents, peroxide stabilizers, desensitizing agents, whiteners, anti-stain agents, breath fresheners, flavorants, sweeteners, colorants, buffers, surfactants, and anti-bacterial agents, with the proviso that if bleaching agents are employed then peroxide stabilizers must also be employed.

13. The method of claim 12, wherein the starch particles are cold cooked, meaning that they have been partially pre-cooked prior to their addition to the organic polyol and, therefore, can be fully cooked at lower temperatures and in less time.

14. The method of claim 12, wherein the starch particles are cooked to a point that they cease to be birefringent and at least some of the boundaries in the particles become indistinct.

15. The method of claim 12, wherein the starch's polymer chains disentangle during cooking and swell at least three fold.

16. The method of claim 12, wherein the starch particles and organic polyols are cooked at a temperature of at least 80° C. for at least about 5 minutes.

17. The method of claim 12, wherein the starch particles and organic polyols are stirred during the cooking step.

18. The method of claim 12, wherein the mixture is cooled prior to the addition of heat labile components.

19. The method of claim 12, wherein the organic polyols are selected from the group consisting of glycerin, propylene glycol, xylitol, sorbitol, mannitol, lactitol, maltitol, erythritol, and mixtures thereof.

20. The method of claim 12, wherein the cooked starch particles are the only gelling agent employed.

* * * * *